US010912538B2

(12) United States Patent
Agano (10) Patent No.: US 10,912,538 B2
(45) Date of Patent: Feb. 9, 2021

(54) ULTRASOUND DIAGNOSTIC APPARATUS AND METHOD OF PRODUCING ULTRASOUND IMAGE (71) Applicant: FUJIFILM Corporation, Tokyo (JP)

(72) Inventor: Toshitaka Agano, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 892 days.

(21) Appl. No.: 14/509,093

(22) Filed: Oct. 8, 2014

(65) Prior Publication Data
US 2015/0025382 A1 Jan. 22, 2015

Related U.S. Application Data (63) Continuation of application No. PCT/JP2013/056969, filed on Mar. 13, 2013.

(30) Foreign Application Priority Data

Apr. 9, 2012 (JP) .................. 2012-088278

(51) Int. Cl.
A61B 8/08 (2006.01)
G01S 7/52 (2006.01)
(Continued)

(52) U.S. Cl.
CPC ............ A61B 8/5292 (2013.01); A61B 8/145 (2013.01); A61B 8/4488 (2013.01); A61B 8/463 (2013.01);
(Continued)

(58) Field of Classification Search
CPC ... G01H 5/00; G01S 7/52036; G01S 7/52049; G01S 7/52073; G01S 7/52074;
(Continued)

(56) References Cited

U.S. PATENT DOCUMENTS 9,110,156 B2 * 8/2015 Kim .................. G01S 7/52049
2002/0091319 A1 * 7/2002 Moehring ........... G01S 7/52046
600/454
(Continued)

FOREIGN PATENT DOCUMENTS

JP 7-323030 A 12/1995
JP 2002-177280 A 6/2002
(Continued)

OTHER PUBLICATIONS

Translation of JP2010207490A (Year: 2010).*
(Continued)

Primary Examiner — Bill Thomson
Assistant Examiner — Helene Bor
(74) Attorney, Agent, or Firm — Birch, Stewart, Kolasch & Birch, LLP (57) ABSTRACT An ultrasound diagnostic apparatus includes an ultrasound image producer which produces an ultrasound image from reception data based on a predetermined set sound speed, a reception data image producer which produces a reception data image representing a luminance image of an ultrasonic echo wavefront from the reception data corresponding to a predetermined range on at least one scan line in the ultrasound image, a sound speed determination unit configured to determine an optimum sound speed based on ultrasound images respectively produced by the ultrasound image producer while changing the predetermined set sound speed, and a controller which makes an ultrasound image for diagnosis produced by the ultrasound image producer and the reception data image produced by the reception data image producer be displayed simultaneously on a display unit based on the optimum sound speed determined by the sound speed determination unit.

18 Claims, 7 Drawing Sheets (51) Int. Cl.
*A61B 8/00* (2006.01)
*A61B 8/14* (2006.01)
*G01H 5/00* (2006.01)

(52) U.S. Cl.
CPC .......... *A61B 8/5207* (2013.01); *A61B 8/5223* (2013.01); *A61B 8/54* (2013.01); *G01S 7/52036* (2013.01); *G01S 7/52049* (2013.01); *G01S 7/52073* (2013.01); *G01S 7/52074* (2013.01); *A61B 8/4494* (2013.01); *A61B 8/5269* (2013.01); *G01H 5/00* (2013.01); *G01S 7/52071* (2013.01)

(58) Field of Classification Search
CPC ... G01S 7/52071; A61B 8/5292; A61B 8/145; A61B 8/4488; A61B 8/463; A61B 8/5207; A61B 8/5223; A61B 8/54; A61B 8/4494; A61B 8/5269
See application file for complete search history.

(56) References Cited

U.S. PATENT DOCUMENTS

| | | | | |
|---|---|---|---|---|
| 2003/0092990 A1* | 5/2003 | Baba | ........................ | A61B 8/00 600/443 |
| 2004/0133106 A1* | 7/2004 | Kakee | .................... | A61B 8/481 600/437 |
| 2008/0242999 A1* | 10/2008 | Kakee | ...................... | A61B 8/00 600/458 |
| 2009/0099451 A1* | 4/2009 | Nakaya | ............... | G01S 7/52046 600/443 |
| 2010/0076312 A1* | 3/2010 | Katsuyama | .............. | A61B 8/00 600/443 |
| 2010/0331692 A1* | 12/2010 | Kakee | ...................... | A61B 8/06 600/443 |
| 2011/0077519 A1* | 3/2011 | Katsuyama | .............. | A61B 8/08 600/443 |

FOREIGN PATENT DOCUMENTS

| | | | |
|---|---|---|---|
| JP | 2011-92686 A | | 6/2002 |
| JP | 2008-264531 A | | 11/2008 |
| JP | 2010207490 A | * | 9/2010 |

OTHER PUBLICATIONS

International Preliminary Report on Patentability and English translation of the Written Opinion of the International Searching Authority (Forms PCT/IB/338, PCT/IB/373 and PCT/ISA/237), dated Oct. 23, 2014, for International Application No. PCT/JP2013/056969.
Japanese Office Action and a partial English translation dated Oct. 20, 2015 for corresponding Application No. 2012-088278.
International Search Report, issued in PCT/JP2013/056969, dated Jun. 18, 2013.

* cited by examiner

RECEPTION DATA IMAGE

OPTIMUM SOUND SPEED
DELAY-CORRECTED DATA IMAGE
1500m/s

FIG. 6

FIG. 7A
PERIPHERAL SOUND SPEED
DELAY-CORRECTED
DATA IMAGE
1480m/s

FIG. 7B
PERIPHERAL SOUND SPEED
DELAY-CORRECTED
DATA IMAGE
1520m/s

ULTRASOUND DIAGNOSTIC APPARATUS AND METHOD OF PRODUCING ULTRASOUND IMAGE

CROSS-REFERENCE TO RELATED APPLICATIONS

This application is a Continuation of PCT International Application No. PCT/JP2013/56969 filed on Mar. 13, 2013, which claims priority under 35 U.S.C. § 119(a) to Japanese Application No. 2012-088278 filed on Apr. 9, 2012. Each of the above application(s) is hereby expressly incorporated by reference, in its entirety, into the present application.

BACKGROUND OF THE INVENTION

The present invention relates to an ultrasound diagnostic apparatus and a method of producing an ultrasound image, and in particular, to an ultrasound diagnostic apparatus which performs an ultrasound image production through transmission and reception of an ultrasonic wave by means of an array transducer of an ultrasound probe.

An ultrasound diagnostic apparatus using an ultrasound image has hitherto been put into practical use in the field of medicine. In general, this type of ultrasound diagnostic apparatus has an ultrasound probe in which an array transducer is installed, and an apparatus body connected to the ultrasound probe. Ultrasonic beams are transmitted from the ultrasound probe toward the inside of a subject, an ultrasonic echo from the subject is received by the ultrasound probe, and reception signals output from the ultrasound probe are electrically processed by the apparatus body to produce an ultrasound image.

In this ultrasound diagnostic apparatus, complicated electrical processing, such as logarithmic compression or delay addition, is carried out for the detected reception signals to obtain a visually easy-to-observe ultrasound image. However, when the complicated processing is performed, there is a risk that valuable information which is inherent in the received ultrasonic echo is lost during the processing.

Accordingly, for example, JP 2002-177280 A suggests an ultrasound diagnostic apparatus in which actual data being processed is extracted and the extracted actual data is displayed in parallel along with an ultrasound image.

However, in the apparatus of JP 2002-177280 A, since the waveform of actual data of one channel among a plurality of channels is merely displayed, even if valuable information is inherent in the actual data, it is difficult for an operator of the ultrasound diagnostic apparatus to grasp new information, which cannot be obtained from the ultrasound image, by observing the waveform.

SUMMARY OF THE INVENTION

The present invention has been accomplished in order to solve the above-described problem in the prior art, and an object of the present invention is to provide an ultrasound diagnostic apparatus and a method of producing an ultrasound image capable of easily grasping information which is inherent in a received ultrasonic echo and which cannot be obtained from an ultrasound image.

An ultrasound diagnostic apparatus according to the present invention comprises an array transducer, a transmission circuit which transmits an ultrasonic beam from the transducer array toward a subject, a reception circuit which electrically processes reception signals output from the transducer array having received an ultrasonic echo from the subject to obtain reception data, a reception data memory which stores the reception data, an ultrasound image producer which produces an ultrasound image from the reception data based on a predetermined set sound speed, a display unit configured to display the ultrasound image produced by the ultrasound image producer, a reception data image producer which produces a reception data image representing a luminance image of an ultrasonic echo wavefront from the reception data corresponding to a predetermined range on at least one scan line in the ultrasound image, a sound speed determination unit configured to determine an optimum sound speed based on ultrasound images respectively produced by the ultrasound image producer while changing the predetermined set sound speed, and a controller which makes an ultrasound image for diagnosis produced by the ultrasound image producer and the reception data image produced by the reception data image producer be displayed simultaneously on the display unit based on the optimum sound speed determined by the sound speed determination unit.

A method of producing an ultrasound image according to the present invention comprises the steps of transmitting an ultrasonic beam from an array transducer toward a subject, electrically processing reception signals output from the array transducer having received an ultrasonic echo from the subject to acquire reception data, producing an ultrasound image from the reception data based on a predetermined set sound speed, determining an optimum sound speed based on ultrasound images respectively produced while changing the predetermined set sound speed, producing an ultrasound image for diagnosis based on the determined optimum sound speed, producing a reception data image representing a luminance image of an ultrasonic echo wavefront from the reception data corresponding to a predetermined range on at least one scan line in the ultrasound image, and simultaneously displaying the ultrasound image for diagnosis and the reception data image on a display unit.

DETAILED DESCRIPTION OF THE INVENTION

Hereinafter, embodiments of the present invention will be described with reference to the accompanying drawings.

Embodiment 1

Figure 1:
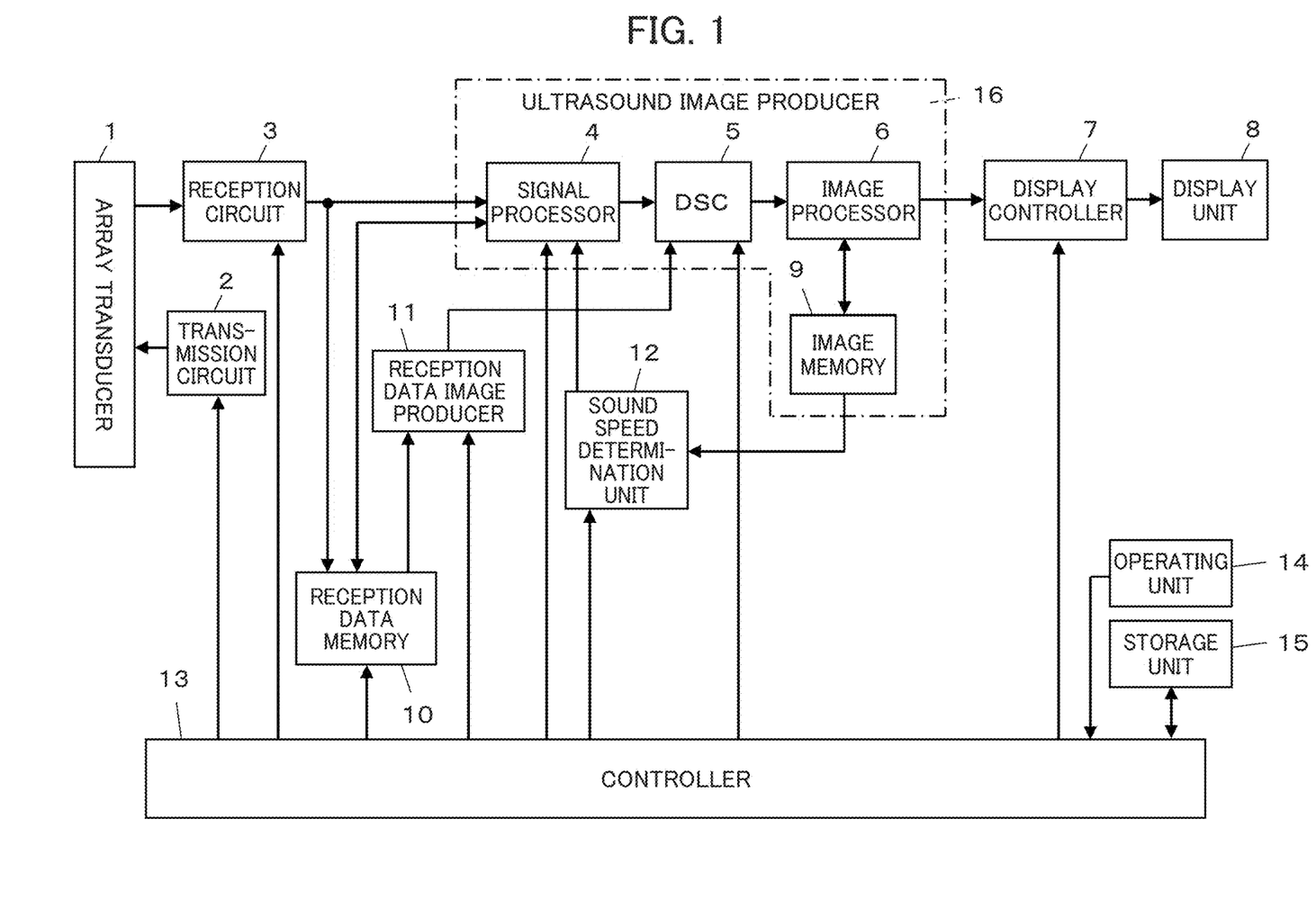
FIG. 1 is a block diagram showing the configuration of an ultrasound diagnostic apparatus according to Embodiment 1 of the present invention.

FIG. 1 shows the configuration of an ultrasound diagnostic apparatus according to Embodiment 1 of the present invention. The ultrasound diagnostic apparatus includes an array transducer 1, and a transmission circuit 2 and a reception circuit 3 are connected to the array transducer 1. A signal processor 4, a DSC (Digital Scan Converter) 5, an image processor 6, a display controller 7, and a display unit 8 are sequentially connected to the reception circuit 3, and an image memory 9 is connected to the image processor 6.

In addition, a reception data memory 10 is connected to the reception circuit 3 and the signal processor 4, a reception data image producer 11 is connected to the reception data memory 10 and the DSC 5, and a sound speed determination unit 12 is connected to the image memory 9 and the signal processor 4. Further, a controller 13 is connected to the transmission circuit 2, the reception circuit 3, the signal processor 4, the DSC 5, the display controller 7, the reception data memory 10, the reception data image producer 11 and the sound speed determination unit 12, and an operating unit 14 and a storage unit 15 are connected to the controller 13.

The array transducer 1 has a plurality of ultrasound transducers arranged in a one-dimensional or two-dimensional array. Each of the plurality of ultrasound transducers transmits an ultrasonic wave in accordance with a driving signal supplied from the transmission circuit 2, receives an ultrasonic echo from the subject, and outputs a reception signal. Each ultrasound transducer is constituted by a vibrator in which electrodes are formed at both ends of a piezoelectric substance formed of, for example, a piezoelectric ceramic represented by PZT (lead zirconate titanate), a polymer piezoelectric element such as PVDF (polyvinylidene fluoride), a piezoelectric single crystal represented by PMN-PT (lead magnesium niobate-lead titanate solid solution), or the like.

If a pulsed or continuous-wave voltage is applied across the electrodes of the vibrator, the piezoelectric substance expands and contracts, whereby pulsed or continuous-wave ultrasonic waves are produced from the respective vibrators and the produced ultrasonic waves are synthesized to form an ultrasonic beam. When receiving propagating ultrasonic waves, the respective vibrators expand and contract to produce electric signals, and the electric signals are output as the reception signals of the ultrasonic waves.

The transmission circuit 2 includes, for example, a plurality of pulse generators. The transmission circuit 2 adjusts the delay amount of each of the driving signals on the basis of a transmission delay pattern selected in response to a control signal from the controller 13 such that ultrasonic waves transmitted from the plurality of ultrasound transducers of the array transducer 1 form an ultrasonic beam, and supplies the adjusted driving signals to the plurality of ultrasound transducers.

The reception circuit 3 amplifies the reception signals transmitted from the respective ultrasound transducers of the array transducer 1, and A/D converts the amplified reception signals to produce digitized reception data of the number of reception channels.

The signal processor 4 produces plural pieces of delay-corrected data by performing respective delay corrections on the plural pieces of reception data produced by reception circuit 3 in accordance with sound speed input from the sound speed determination unit 12, and performs reception focus processing by adding these plural pieces of delay-corrected data. With this reception focus processing, the focus of the ultrasonic echo is narrowed down to produce a sound ray signal. Further, the signal processor 4 performs correction of attenuation due to distance on the sound ray signal depending on the depth of the reflection position of the ultrasonic wave, and then performs envelope detection processing to produce a B-mode image signal which is tomographic image information relating to the tissues of the subject.

The DSC 5 converts (raster-converts) the B-mode image signal produced by the signal processor 4 to an image signal based on a normal television signal scanning system.

The image processor 6 performs various necessary image processing, such as gradation processing, on the B-mode image signal input from the DSC 5, and outputs the processed B-mode image signal to the display controller 7 or stores the processed B-mode image signal in the image memory 9.

The signal processor 4, the DSC 5, the image processor 6, and the image memory 9 constitute an ultrasound image producer 16.

The display controller 7 causes the display unit 8 to display an ultrasound diagnostic image on the basis of the B-mode image signal subjected to the image processing by the image processor 6.

The display unit 8 includes, for example, a display device such as an LCD, and displays the ultrasound diagnostic image under the control of the display controller 7.

The reception data memory 10 sequentially stores reception data output from the reception circuit 3, and also stores delay-corrected data produced by the signal processor 4.

The reception data image producer 11 produces a reception data image signal and a delay-corrected data image signal, both of which represent luminance images of an ultrasonic echo wavefront, from reception data and delay-corrected data stored in the reception data memory 10, respectively, under the control of the controller 13.

The sound speed determination unit 12 provides a predetermined set sound speed to the signal processor 4, and also analyzes the B-mode image signal produced by the ultrasound image producer 16 and stored in the image memory 9 while changing the set sound speed to determine a sound speed which gives the highest contrast or sharpness to the image to be an optimum sound speed.

The controller 13 controls the respective constituents of the ultrasound diagnostic apparatus on the basis of commands input from the operation unit 14 by an operator.

The operating unit 14 is used when the operator performs an input operation, and may be constituted by a keyboard, a mouse, a trackball, a touch panel, or the like.

The storage unit 15 stores an operation program or the like, and may be constituted by a recording medium such as a hard disk, a flexible disk, an MO, an MT, a RAM, a CD-ROM, a DVD-ROM, an SD card, a CF card and a USB memory, a server, or the like.

The signal processor 4, the DSC 5, the image processor 6, the display controller 7, the reception data image producer 11, and the sound speed determination unit 12 are constituted by a CPU and an operation program which causes the CPU to perform various processing, but these may be constituted by digital circuits.

Next, the operation of Embodiment 1 will be described.

First, ultrasonic waves are transmitted from the plurality of ultrasound transducers of the array transducer 1 according to a driving signal supplied from the transmission circuit 2, a reception signal is output from each ultrasound transducer with the reception of an ultrasonic echo from the subject to the reception circuit 3, and reception data is produced by the reception circuit 3 and is sequentially stored in the reception data memory 10.

Here, a predetermined first set sound speed C1 is input from the sound speed determination unit 12 to the signal processor 4, and the signal processor 4 reads out the plural pieces of reception data stored in the reception data memory 10 and performs delay correction thereon according to the sound speed C1 input from the sound speed determination unit 12 to produce plural pieces of delay-corrected data. The plural pieces of delay-corrected data are sequentially stored in the reception data memory 10, and the signal processor 4 adds the plural pieces of delay-corrected data to produce a sound ray signal, and performs the attenuation correction and the envelope detection processing on the sound ray signal to produce a B-mode image signal. The B-mode image signal is raster-converted by the DSC 5, is subjected to various kinds of image processing by the image processor 6, and is then stored in the image memory 9.

If the B-mode image signal corresponding to the first set sound speed C1 given from the sound speed determination unit 12 is produced by the ultrasound image producer 16 and is stored in the image memory 9, the sound speed determination unit 12 outputs a second set sound speed C2 which is different from the first set sound speed C1 by a predetermined amount to the signal processor 4. With this, similarly to the above, a B-mode image signal corresponding to the second set sound speed C2 is produced by the ultrasound image producer 16 and is stored in the image memory 9.

In this way, a plurality of set sound speeds C1 to Cn are sequentially given from the sound speed determination unit 12 to the signal processor 4, and a plurality of B-mode image signals corresponding to the set sound speeds C1 to Cn are produced by the ultrasound image producer 16 and are stored in the image memory 9. Then, the sound speed determination unit 12 analyzes the B-mode image signals stored in the image memory 9 and determines a sound speed which gives the highest contrast or sharpness to the image to be an optimum sound speed Cp. At this time, the analysis of the B-mode image signal is performed for each of a plurality of divided regions of the ultrasound image, and the determination of the optimum sound speed Cp is performed for each divided region.

Figure 2:
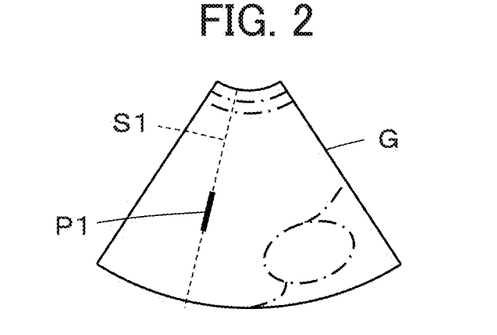
FIG. 2 is a diagram showing an ultrasound image in Embodiment 1, in which a predetermined range is set on one scan line.

Next, the optimum sound speed Cp of each divided region is output from the sound speed determination unit 12 to the signal processor 4, and a B-mode image signal is produced by the ultrasound image producer 16 using the optimum sound speed Cp of each divided region. That is, delay correction is performed on the reception data read out from the reception data memory 10 according to the optimum sound speed Cp of each divided region to produce delay-corrected data, the delay-corrected data is stored in the reception data memory 10, and a B-mode image signal corresponding to the optimum sound speed Cp is produced based on the delay-corrected data. The B-mode image signal is output to the display controller 7, and as shown in FIG. 2, an ultrasound image G for diagnosis having the optimum sound speed is displayed on the display unit 8.

Here, the operator operates the operating unit 14 to designate one scan line S1 and a predetermined range P1 on the scan line S1 in the ultrasound image G displayed on the display unit 8.

Figure 3:
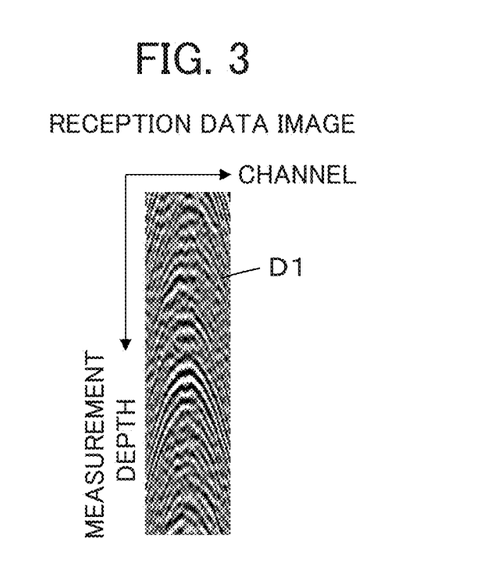
FIG. 3 is a diagram showing a reception data image corresponding to the predetermined range shown in FIG. 2.

If the predetermined range P1 is designated, a command of reception data image production is output from the controller 13 to the reception data image producer 11, plural pieces of reception data corresponding to the predetermined range P1 are read out from the reception data memory 10 by the reception data image producer 11, and a reception data image signal is produced using these plural pieces of reception data. The reception data image signal is raster-converted by the DSC 5, is subject to various kinds of image processing by the image processor 6, and is then output to the display controller 7 to display a reception data image D1 on the display unit 8, as shown in FIG. 3.

The reception data image D1 is obtained by imaging reception data from each ultrasound transducer which receives an ultrasonic echo from the predetermined range P1, and the imaging is performed such that the horizontal axis direction indicates the number of channels of each ultrasound transducer of the array transducer 1 and the vertical axis direction indicates the measurement depth direction in the predetermined range P1 on the scan line S1. The reception data image D1 represents a luminance image of an ultrasonic echo wavefront.

Figure 4:
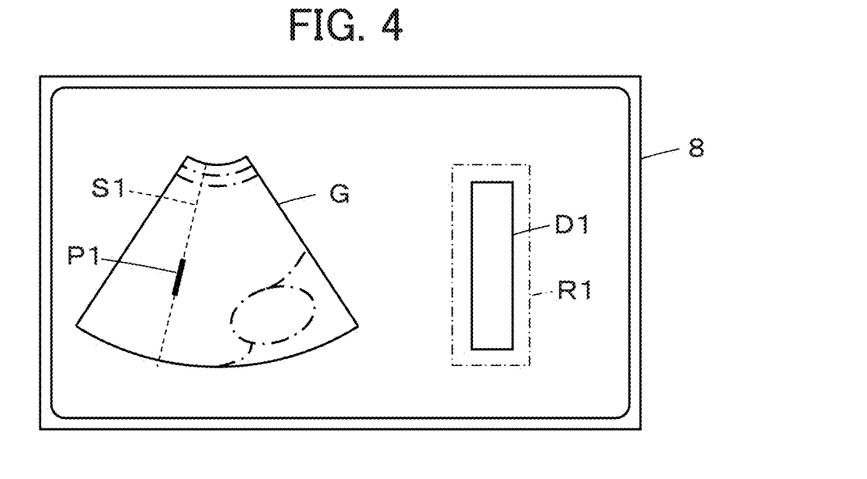
FIG. 4 is a diagram showing the display contents of a display unit in Embodiment 1.

In this way, as shown in FIG. 4, the ultrasound image G for diagnosis is displayed on the display unit 8, and the reception data image D1 is displayed in a data image display region R1 divided adjacent to the ultrasound image G.

As described above, according to Embodiment 1, not only a high-quality ultrasound image G can be obtained using the optimum sound speed Cp determined for each divided region, but also a reception data image D1 representing a luminance image of an ultrasonic echo wavefront is displayed using reception data corresponding to a designated predetermined range P1, whereby it is possible to easily grasp information which is inherent in the ultrasonic echo and cannot be obtained from the ultrasound image.

Embodiment 2

In Embodiment 1, since delay-corrected data obtained through delay correction in accordance with the optimum sound speed Cp of each divided region for reception data by the signal processor 4 is stored in the reception data memory 10, it is possible to produce an optimum sound speed delay-corrected data image using the delay-corrected data.

Figure 5:
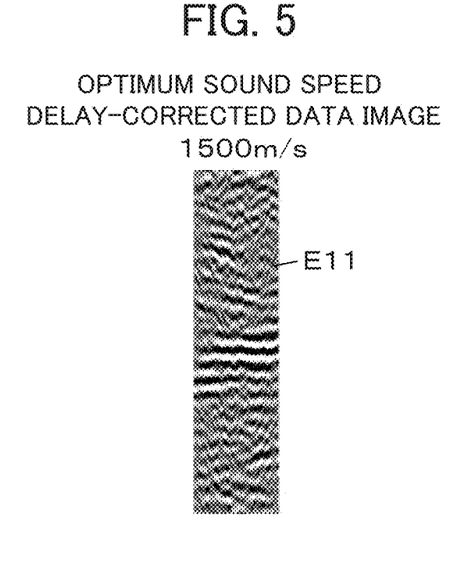
FIG. 5 is a diagram showing an optimum sound speed delay-corrected data image to be displayed in Embodiment 2.

In Embodiment 2, similarly to the production of the reception data image D1, first, delay-corrected data subjected to delay correction with optimum sound speed is read out from the reception data memory 10 and an optimum sound speed delay-corrected data image signal is produced by the reception data image producer 11. The optimum sound speed delay-corrected data image signal is raster-converted by the DSC 5, is subjected to various kinds of image processing by the image processor 6, and is then output to the display controller 7 to display an optimum sound speed delay-corrected data image E11, as shown in FIG. 5. In FIG. 5, it is assumed that the optimum sound speed in the predetermined range P1 is 1500 m/s.

The optimum sound speed delay-corrected data image E11 is obtained by imaging the data obtained after delay correction of reception data from each ultrasound transducer which receives an ultrasound echo from the predetermined range P1, and similarly to the reception data image D1, the imaging is performed such that the horizontal axis direction indicates the number of channels of each ultrasound transducer of the array transducer 1 and the vertical axis direction indicates the measurement depth direction in the predetermined range P1 on the scan line S1. The optimum sound speed delay-corrected data image E11 represents a luminance image of an ultrasonic echo wavefront.

Figure 6:
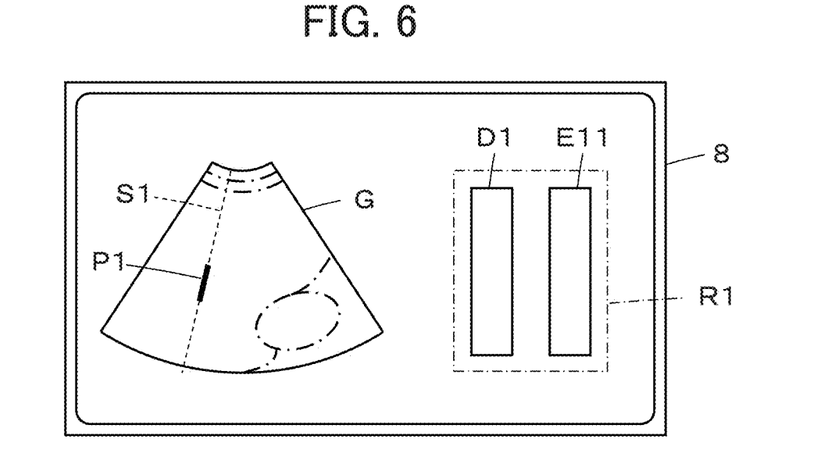
FIG. 6 is a diagram showing the display contents of a display unit in Embodiment 2.

Then, as shown in FIG. 6, the reception data image D1 and the optimum sound speed delay-corrected data image E11 are displayed in the data image display region R1 divided adjacent to the ultrasound image G. At this time, the value of the optimum sound speed, 1500 m/s, is also displayed along with the optimum sound speed delay-corrected data image E11.

The operator confirms the optimum sound speed delay-corrected data image E11 subjected to delay correction with the optimum sound speed along with the confirmation of the reception data image D1, thereby more easily grasping information inherent in the ultrasonic echo.

In the determination of the optimum sound speed, plural pieces of delay-corrected data obtained through respective delay corrections according to the set sound speeds which are changed by a predetermined amount by the sound speed determination unit 12 are stored in the reception data memory 10. Accordingly, two peripheral sound speed delay-corrected data images may be produced using two pieces of delay-corrected data subjected to delay corrections with peripheral sound speeds before and after the optimum sound speed.

Figure 7A:
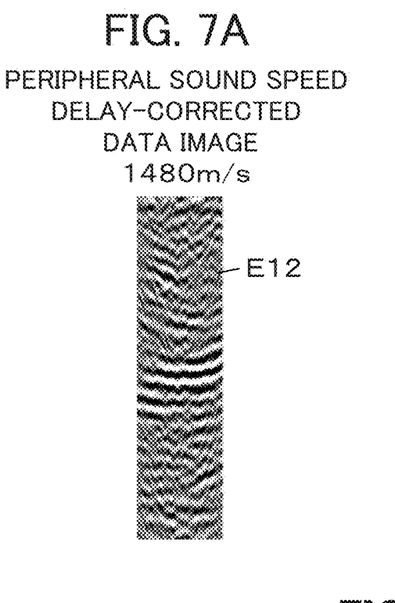
FIGS. 7A and 7B are diagrams showing a peripheral sound speed delay-corrected data image to be displayed in a modification example of Embodiment 2.
Figure 7B:
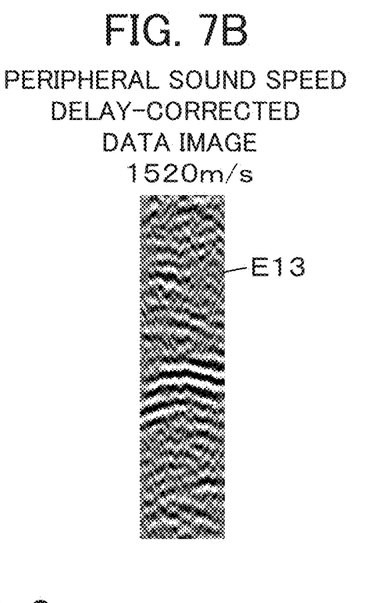

That is, two pieces of delay-corrected data subjected to delay corrections with the peripheral sound speeds before and after the optimum sound speed are read out from the reception data memory 10 and the peripheral sound speed delay-corrected data image signals are produced by the reception data image producer 11. The peripheral sound speed delay-corrected data image signals are raster-converted by the DSC 5, are subjected to various kinds of image processing by the image processor 6, and are then output to the display controller 7 to display peripheral sound speed delay-corrected data images E12 and E13, as shown in FIGS. 7A and 7B. In FIGS. 7A and 7B, the peripheral sound speed delay-corrected data image E12 corresponding to a peripheral sound speed of 1480 m/s which is lower than the optimum sound speed of 1500 m/s in the predetermined range P1 by a predetermined amount of 20 m/s, and the peripheral sound speed delay-corrected data image E13 corresponding to a peripheral sound speed of 1520 m/s which is higher than the optimum sound speed of 1500 m/s by a predetermined amount of 20 m/s are shown.

The peripheral sound speed delay-corrected data images E12 and E13 are obtained by imaging the two pieces of data obtained after respective delay corrections of reception data from each ultrasound transducer which receives an ultrasonic echo from the predetermined range P1, and similarly to the above, the imaging is performed such that the horizontal axis direction indicates the number of channels of each ultrasound transducer of the array transducer 1 and the vertical axis direction indicates the measurement depth direction in the predetermined range P1 on the scan line S1. Both the peripheral sound speed delay-corrected data images E12 and E13 represent luminance images of an ultrasonic echo wavefront.

Figure 8:
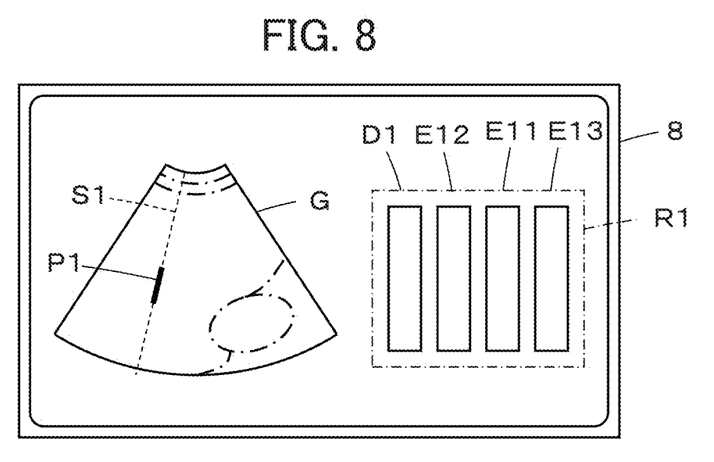
FIG. 8 is a diagram showing the display contents of a display unit in the modification example of Embodiment 2.

Then, as shown in FIG. 8, the peripheral sound speed delay-corrected data images E12 and E13 are displayed in the data image display region R1 divided adjacent to the ultrasound image G along with the reception data image D1 and the optimum sound speed delay-corrected data image E11. At this time, the values of the peripheral sound speeds, 1480 m/s and 1520 m/s, are respectively displayed along with the peripheral sound speed delay-corrected data images E12 and E13.

The operator can observe the sound speed tendency at a local position on the scan line S1 with reference to the peripheral sound speed delay-corrected data images E12 and E13, and can recognize information inherent in the ultrasonic echo in more detail.

Embodiment 3

In Embodiments 1 and 2, one predetermined range P1 is designated in the ultrasound image G by the operator, and the reception data image D1 corresponding to the predetermined range P1 is produced and displayed on the display unit 8, or the data images including the reception data image D1, the optimum sound speed delay-corrected data image E11, and further the peripheral sound speed delay-corrected data images E12 and E13 which correspond to the predetermined range P1 are produced and displayed on the display unit 8. But, a plurality of predetermined ranges may be designated in the ultrasound image G and data images corresponding to the respective predetermined ranges may be produced.

Figure 9:
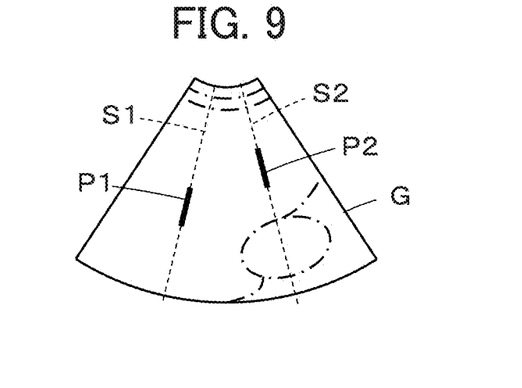
FIG. 9 is a diagram showing a B-mode image in Embodiment 3, in which a predetermined range is set on each of two scan lines.

For example, as shown in FIG. 9, two ranges of a predetermined range P1 on a scan line S1 and a predetermined range P2 on a scan line S2 in ultrasound image G may be designated, and data images corresponding to the predetermined range P1 and data images corresponding to the predetermined range P2 may be produced and displayed on the display unit 8.

Figure 10:
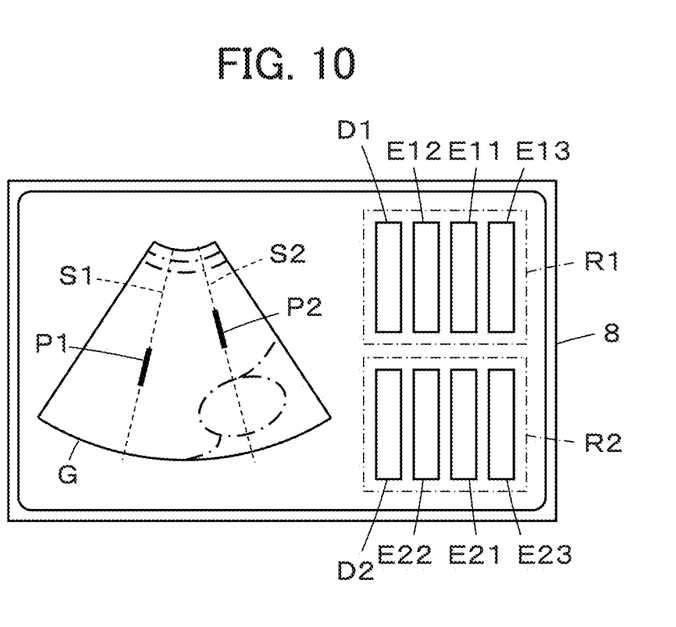
FIG. 10 is a diagram showing the display contents of a display unit in Embodiment 3.

As shown in FIG. 10, two data image display regions R1 and R2 are divided adjacent to the ultrasound image G of the display unit 8, a reception data image D1, an optimum sound speed delay-corrected data image E11, and peripheral sound speed delay-corrected data images E12 and E13 corresponding to the predetermined range P1 are displayed in the data image display region R1, and a reception data image D2, an optimum sound speed delay-corrected data image E21, and peripheral sound speed delay-corrected data images E22 and E23 corresponding to the predetermined range P2 are displayed in the data image display region R2.

In this way, data images corresponding to a plurality of predetermined ranges are displayed, whereby it is possible to compare and observe the plurality of predetermined ranges simultaneously and to perform diagnosis with higher precision.

In FIG. 10, the reception data image, the optimum sound speed delay-corrected data image, and the peripheral sound speed delay-corrected data images are displayed for each of the two predetermined ranges P1 and P2, but as a data image, only a reception data image may be produced and displayed for each predetermined range, or only a reception data image and an optimum sound speed delay-corrected data image may be produced and displayed for each predetermined range.

In addition, the two predetermined ranges P1 and P2 are not necessarily positioned on the different scan lines S1 and S2, and may be positioned on the same scan line. The number of predetermined ranges is not limited to two, and three or more predetermined ranges may be designated and data images may be produced and displayed for respective predetermined ranges. Instead of simultaneously displaying the data images of the two predetermined ranges P1 and P2, the data images of the predetermined range P1 or the data images of the predetermined range P2 may be switched and displayed, thereby securing a sufficient display area of the data images.

Embodiment 4

Figure 11:
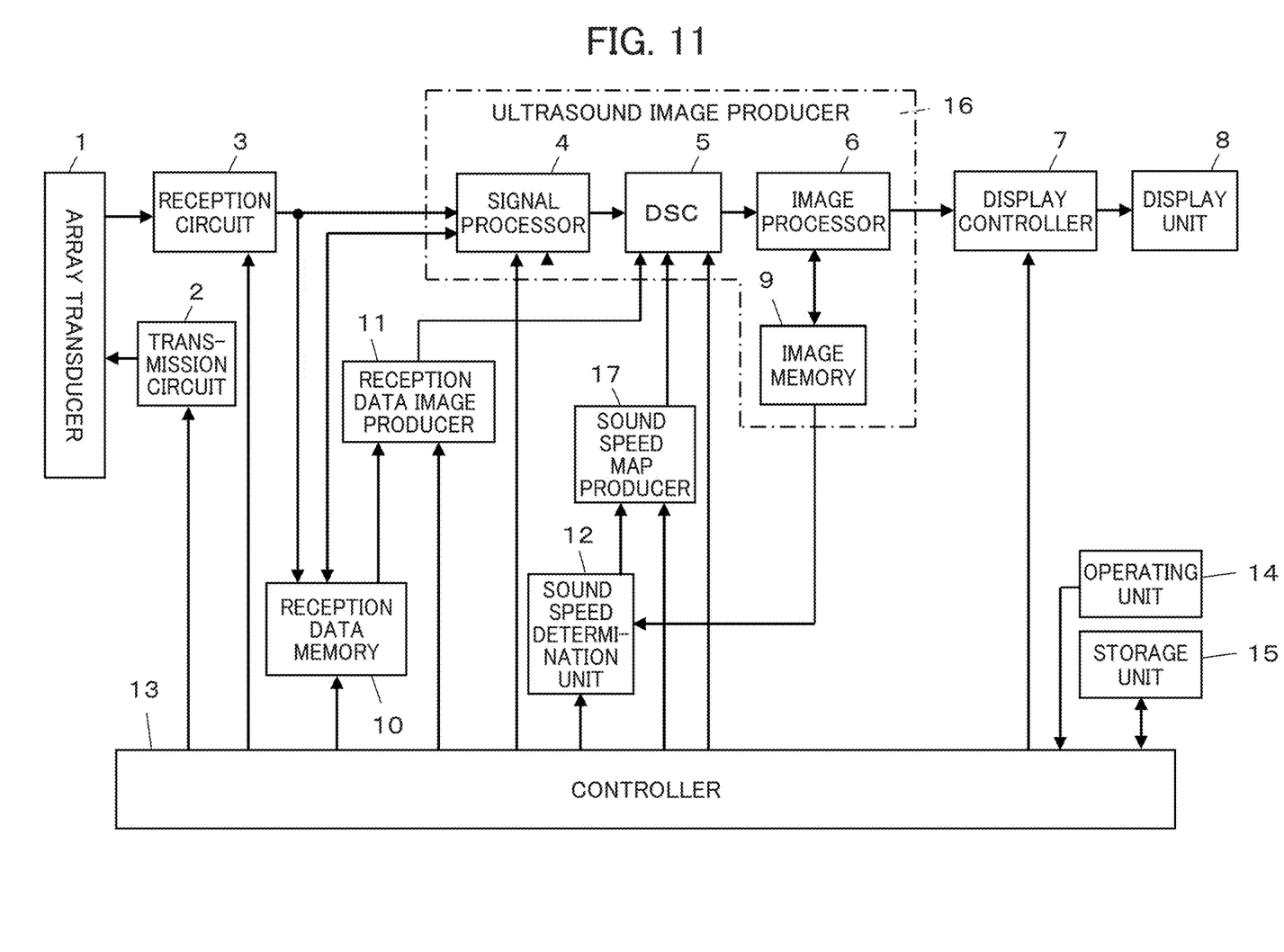
FIG. 11 is a block diagram showing the configuration of an ultrasound diagnostic apparatus according to Embodiment 4.

FIG. 11 shows the configuration of an ultrasound diagnostic apparatus according to Embodiment 4. The ultrasound diagnostic apparatus further includes a sound speed map producer 17 in the apparatus of Embodiment 1 shown in FIG. 1. The sound speed map producer 17 is connected to the reception data memory 10, the sound speed determination unit 12, and the DSC 5, and is also connected to the controller 13.

The sound speed map producer 17 calculates a local sound speed value in a tissue of a subject to be diagnosed based on the reception data stored in the reception data memory 10 under the control of the controller 13, and produces a sound speed map.

Here, the calculation of the local sound speed value can be performed by the method described in, for example, JP 2010-99452 A filed by the applicant of the present application.

Figure 12A:
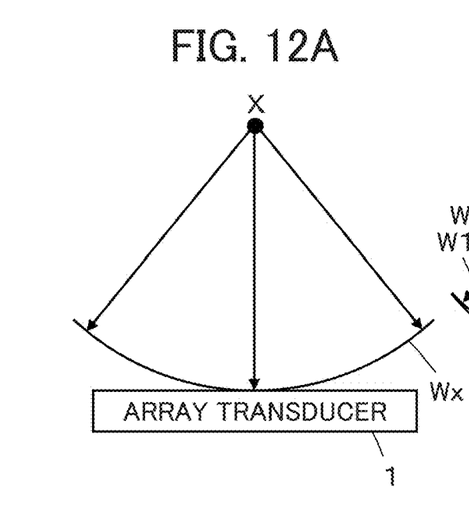
FIGS. 12A and 12B are diagrams schematically showing the principle of sound speed calculation in Embodiment 4.
Figure 12B:
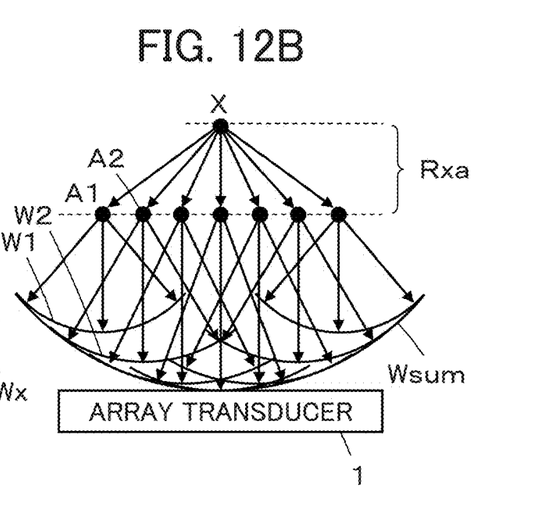

This method is based on the fact that as shown in FIG. 12A, when focusing on a reception wave Wx reaching the array transducer 1 from a lattice point X to be a reflection point of a subject in transmitting an ultrasonic wave into the subject, as shown in FIG. 12B, if a plurality of lattice points A1, A2, . . . are arranged at regular intervals at positions shallower than the lattice point X, that is, at positions closer to the array transducer 1, a synthetic wave Wsum of reception waves W1, W2, . . . from the plurality of lattice points A1, A2, . . . which receive a reception wave from the lattice point X matches the reception wave Wx from the lattice point X by Huygen's principle, and in the method, a local sound speed value at the lattice point X is calculated using the fact.

First, the optimum sound speed value is calculated for all lattice points X, A1, A2, . . . . Here, the optimum sound speed value is a sound speed value which gives the highest contrast or sharpness to an ultrasound image when focus calculation and imaging are performed for each lattice point based on the set sound speed to form an ultrasound image and then the set sound speed is variously changed, and in Embodiment 4, the value of the optimum sound speed determined by the sound speed determination unit 12 can be used.

Next, the waveform of a virtual reception wave Wx radiated from the lattice point X is calculated using the optimum sound speed value for the lattice point X.

Further, a virtual synthetic wave Wsum of reception waves W1, W2, . . . from the respective lattice points A1, A2, . . . is calculated while variously changing a virtual local sound speed value V at the lattice point X. At this time, it is assumed that the sound speed is uniform in a region Rxa between the lattice point X and each of the lattice points A1, A2, . . . , and is equal to the local sound speed value V at the lattice point X. The time until an ultrasonic wave propagating from the lattice point X reaches the each of the lattice points A1, A2, . . . becomes XA1/V, XA2/V, . . . . Here, XA1, XA2, . . . refer to the distances between the respective lattice points A1, A2, . . . and the lattice point X. Accordingly, the virtual synthetic wave Wsum can be calculated by synthesizing reflected waves radiated from the lattice points A1, A2, . . . while being delayed by the time XA1/V, XA2/V, . . . .

Next, errors between a plurality of virtual synthetic waves Wsum which are calculated by variously changing the virtual local sound speed value V at the lattice point X and the virtual reception wave Wx from the lattice point X are calculated, and the virtual local sound speed value V having the minimum error is determined to be the local sound speed value at the lattice point X. Here, as the calculation method of the error between the virtual synthetic wave Wsum and the virtual reception wave Wx from the lattice point X, a method which calculates the cross-correlation therebetween, a method which multiplies the reception wave Wx and the delay obtained from the synthetic wave Wsum to perform phase matching addition, a method which multiplies the synthetic wave Wsum and the delay obtained from the reception wave Wx to perform phase matching addition, or the like may be adopted.

In this manner, it is possible to calculate the local sound speed value in the subject with high precision based on the reception data stored in the reception data memory 10. Similarly, it is possible to produce a sound speed map representing the distribution of the local sound speed value in a set region of interest.

Next, the operation of Embodiment 4 will be described.

Figure 13:
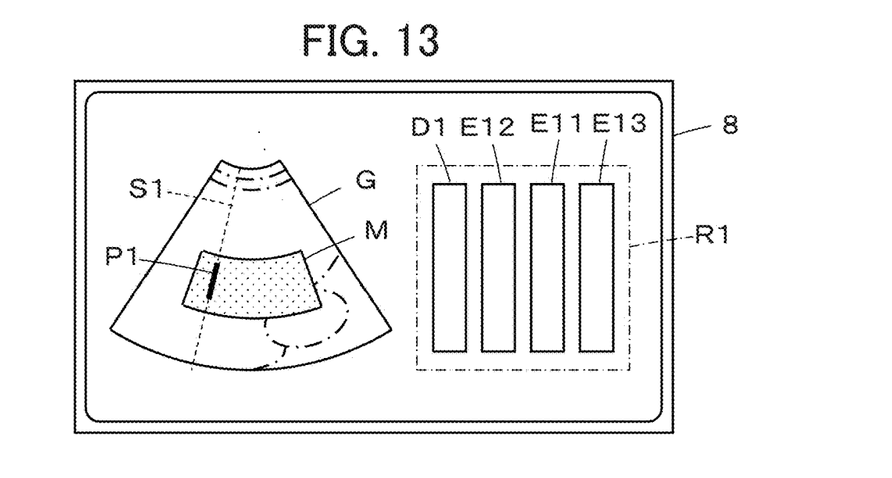
FIG. 13 is a diagram showing the display contents of a display unit in Embodiment 4.

First, similarly to Embodiment 2, as shown in FIG. 13, the ultrasound image G is displayed on the display unit 8, and the reception data image D1, the optimum sound speed delay-corrected data image E11, and the peripheral sound speed delay-corrected data image E12 and E13 are displayed in the data image display region R1 divided adjacent to the ultrasound image G.

Here, if the operator operates the operating unit 14 to set a region of interest on the ultrasound image G, the sound speed map producer 17 produces a sound speed map in the region of interest based on the reception data stored in the reception data memory 10. The sound speed map is sent from the sound speed map producer 17 to the DSC 5, and is displayed on the ultrasound image G of the display unit 8 in a superposed manner as a sound speed map image M through the image processor 6 and the display controller 7. As the sound speed map image M, for example, a map in which a local sound speed value of each place in a region of interest is displayed in color may be used.

In this way, not only the data images, such as the reception data image D1, but also the sound speed map image M are displayed along with the ultrasound image G, whereby it becomes easy to search for a position to be fully observed based on the sound speed distribution, and thus, it is possible to improve the precision and efficiency of diagnosis.

Figure 14:
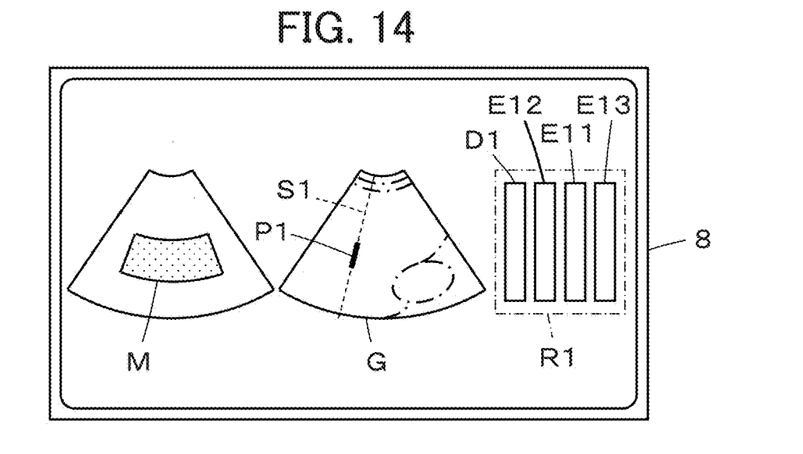
FIG. 14 is a diagram showing the display contents of a display unit in a modification example of Embodiment 4.

In Embodiment 4, the sound speed map image M is displayed on the ultrasound image G in a superposed manner, but as shown in FIG. 14, the sound speed map image M may be displayed in parallel with the ultrasound image G on the display unit 8.

What is claimed is:
1. An ultrasound diagnostic apparatus comprising:
an array transducer;
a transmission circuit which transmits an ultrasonic beam from the transducer array toward a subject;
a reception circuit which electrically digitizes reception signals output from the transducer array having received an ultrasonic echo from the subject to obtain reception data;

a reception data memory which stores the reception data;
a display device; and
a central processing unit (CPU) and an operation program causing the CPU
to produce a tomographic ultrasound image by performing reception focus processing on the reception data based on a predetermined set sound speed to produce sound ray signals;
to determine an optimum sound speed based on tomographic ultrasound images respectively produced while changing the predetermined set sound speed, the optimum sound speed giving the highest contrast or sharpness to an image;
to produce a reception data image, representing a luminance image of an ultrasonic echo wavefront, based on the reception data stored in the reception data memory corresponding to a predetermined distance range on at least one scan line in the tomographic ultrasound image, the reception data image representing the reception data itself and being different from the tomographic ultrasound image; and
to allow a tomographic ultrasound image for diagnosis produced based on the determined optimum sound speed and the produced reception data image to be displayed simultaneously on the display device.

2. The ultrasound diagnostic apparatus according to claim 1,
wherein the CPU performs delay correction on the reception data at the predetermined sound speed to produce delay-corrected data,
produces an optimum sound speed delay-corrected data image from optimum sound speed delay-corrected data produced based on the determined optimum sound speed, and makes the produced optimum sound speed delay-corrected data image be displayed on the display device along with the tomographic ultrasound image for diagnosis and the reception data image.

3. The ultrasound diagnostic apparatus according to claim 2,
wherein the CPU produces a peripheral sound speed delay-corrected data image from peripheral sound speed delay-corrected data produced based on a peripheral sound speed of the optimum sound speed determined and makes the produced peripheral sound speed delay-corrected data image be displayed on the display device along with the tomographic ultrasound image for diagnosis, the reception data image, and the optimum sound speed delay-corrected data image.

4. The ultrasound diagnostic apparatus according to claim 1, further comprising an operating device configured to designate the predetermined distance range by an operator.

5. The ultrasound diagnostic apparatus according to claim 4,
wherein a plurality of predetermined distance ranges are designated on the same scan line or on a plurality of scan lines through the operating unit, and
the CPU makes a plurality of reception data images produced correspondingly to the plurality of predetermined distance ranges be displayed on the display device.

6. The ultrasound diagnostic apparatus according to claim 5,
wherein the CPU makes a plurality of optimum sound speed delay-corrected data images produced correspondingly to the plurality of predetermined distance ranges be displayed on the display device.

7. The ultrasound diagnostic apparatus according to claim 6,
wherein the CPU makes a plurality of peripheral sound speed delay-corrected data images produced correspondingly to the plurality of predetermined distance ranges be displayed on the display device.

8. The ultrasound diagnostic apparatus according to claim 1,
wherein the CPU determines an optimum sound speed for each of a plurality of divided regions of the tomographic ultrasound image.

9. The ultrasound diagnostic apparatus according to claim 8,
wherein the CPU produces a sound speed map based on the determined optimum sound speed of each divided region, and
makes the produced sound speed map be displayed on the display device such that the sound speed map is displayed on the ultrasound tomographic image for diagnosis in a superposed manner or the sound speed map is displayed in parallel with the ultrasound tomographic image for diagnosis.

10. A method of producing an ultrasound image, the method comprising the steps of:
transmitting an ultrasonic beam from an array transducer toward a subject;
electrically digitizing reception signals output from the array transducer having received an ultrasonic echo from the subject to acquire reception data;
producing a tomographic ultrasound image by performing reception focus processing on the reception data based on a predetermined set sound speed to produce sound ray signals;
determining an optimum sound speed based on tomographic ultrasound images respectively produced while changing the predetermined set sound speed, the optimum sound speed giving the highest contrast or sharpness to an image;
producing a tomographic ultrasound image for diagnosis based on the determined optimum sound speed;
producing a reception data image, representing a luminance image of an ultrasonic echo wavefront, based on the reception data corresponding to a predetermined distance range on at least one scan line in the tomographic ultrasound image, the reception data image representing the reception data itself and being different from the tomographic ultrasound image; and
simultaneously displaying the tomographic ultrasound image for diagnosis and the reception data image on a display device.

11. The method of producing an ultrasound image according to claim 10, further comprising the steps of:
producing optimum sound speed delay-corrected data by performing delay corrections on the reception data in accordance with the determined optimum sound speed;
producing an optimum sound speed delay-corrected data image from the produced optimum sound speed delay-corrected data; and
displaying the produced optimum sound speed delay-corrected data image along with the ultrasound tomographic image for diagnosis and the reception data image on the display device.

12. The method of producing an ultrasound image according to claim 11, further comprising the steps of:
producing peripheral sound speed delay-corrected data by performing delay corrections on the reception data in accordance with a peripheral sound speed of the determined optimum sound speed;

producing a peripheral sound speed delay-corrected data image from the produced peripheral sound speed delay-corrected data; and displaying the produced peripheral sound speed delay-corrected data image along with the ultrasound tomographic image for diagnosis, the reception data image and the optimum sound speed delay-corrected data image on the display device.

13. The method of producing an ultrasound image according to claim 10, further comprising the steps of:

designating a plurality of predetermined distance ranges on the same scan line or on a plurality of scan lines; and displaying a plurality of reception data images produced corresponding to the plurality of predetermined distance ranges on the display device.

14. The method of producing an ultrasound image according to claim 13, further comprising the steps of:

producing a plurality of optimum sound speed delay-corrected data images corresponding to the plurality of predetermined distance ranges; and displaying the plurality of optimum sound speed delay-corrected data images on the display device.

15. The method of producing an ultrasound image according to claim 14, further comprising the steps of:

producing a plurality of peripheral sound speed delay-corrected data images corresponding to the plurality of predetermined distance ranges; and displaying the plurality of peripheral sound speed delay-corrected data images on the display device.

16. The method of producing an ultrasound image according to claim 10, wherein determining of the optimum sound speed is performed for each of a plurality of divided regions of the ultrasound tomographic image.

17. The method of producing an ultrasound image according to claim 16, further comprising the steps of:

producing a sound speed map based on the optimum sound speed of each divided region; and displaying the produced sound speed map on the display device such that the sound speed map is displayed on the ultrasound tomographic image for diagnosis in a superposed manner.

18. The method of producing an ultrasound image according to claim 16, further comprising the steps of:

producing a sound speed map based on the optimum sound speed of each divided region; and displaying the produced sound speed map on the display device such that the sound speed map is displayed in parallel with the ultrasound tomographic image for diagnosis.

* * * * *